United States Patent [19]
Heimansohn

[11] 3,958,333
[45] May 25, 1976

[54] ARTIFICIAL TEETH WITH LOCATING LUGS AND METHOD FOR USING SAME

[75] Inventor: Henry C. Heimansohn, Danville, Ind.

[73] Assignee: Indiana University Foundation, Bloomington, Ind.

[22] Filed: Mar. 6, 1975

[21] Appl. No.: 556,168

Related U.S. Application Data
[63] Continuation-in-part of Ser. No. 532,513, Dec. 13, 1974.

[52] U.S. Cl. ................................................. 32/2
[51] Int. Cl.² .................................... A61C 13/00
[58] Field of Search ............. 32/2, 8, 10 R; 264/18, 264/17, 16; 249/54

[56] References Cited
UNITED STATES PATENTS

| | | | |
|---|---|---|---|
| 2,466,727 | 4/1949 | Morgan | 32/2 |
| 2,585,858 | 2/1952 | Schwartz | 32/10 R |
| 2,893,054 | 7/1959 | Schwartz | 32/2 X |
| 3,251,909 | 5/1966 | Pickards et al. | 32/2 X |

*Primary Examiner*—Louis G. Mancene
*Assistant Examiner*—Jack Q. Lever
*Attorney, Agent, or Firm*—Jenkins, Hanley & Coffey

[57] ABSTRACT

Artificial teeth for use in a denture comprising a denture base and a plurality of teeth anchored in the denture base, each tooth having a base portion providing a ridge lap surface and an occlusal portion providing an occlusal surface, wherein the improvement comprises one or more lugs extending outwardly from each tooth intermediate its occlusal surface and the ridge lap surface to serve as a locating lug or tab for positioning the tooth in the mold in which the denture base is formed on the base portions of the teeth. These locating lugs or tabs or at least those which are not embedded in the denture base are removed by grinding and polishing.

8 Claims, 16 Drawing Figures

ARTIFICIAL TEETH WITH LOCATING LUGS AND METHOD FOR USING SAME

This is a continuation-in-part application based upon my prior filed application Ser. No. 532,513 filed Dec. 13, 1974.

The present invention relates to dentures and particularly to the provision of a resilient artificial tooth for use in dentures as well as an artificial tooth having one or more lugs or locating tabs projecting therefrom carefully to position the tooth in the mold in which the denture base is formed.

Artificial denture teeth have been about the same for approximately one hundred seventy years. Dentures have consisted of hard substances, shaped like teeth, permanently fastened to denture bases. Real human teeth represent individual units with roots in the jawbone and possessing slight individual vertical movement upon mastication. Human teeth are much more stable than dentures because they are individually anchored in the jawbone.

Another problem with dentures has to do with the requirement for very precisely locating each tooth in the mold in which the denture base is formed and connected to the base portions of the artificial teeth.

My present invention provides an artificial tooth for a denture, the occlusal portion of that tooth having resiliently resisted movement relative to the base portion. In a set of dentures, including upper and lower dentures, I could provide eight resilient lower posterior teeth (four on each side) that would have vertical individual movement of occlusal (biting) surfaces concurrently with tipping of the occlusal surfaces.

The prior art has suggested several forms of resilient artificial teeth. Such patents as the following United States patents appear to be representative of the prior art: U.S. Pat. No. 1,105,476 issued July 28, 1914; U.S. Pat No. 2,577,769 issued Dec. 11, 1951; U.S. Pat. No. 3,104,465 issued Sept. 24, 1963; U.S. Pat. No. 3,241,238 issued Mar. 22, 1966; U.S. Pat. No. 3,327,392 issued June 27, 1967; U.S. Pat. No. 3,423,831 issued Jan. 28, 1969; U.S. Pat. No. 3,517,443 issued June 30, 1970; U.S. Pat. No. 3,827,145 issued Aug. 6, 1974; and U.S. Pat. No. 3,826,002 issued July 30, 1974.

I submit that the prior art of which I am aware does not disclose nor suggest an acceptable resilient artificial tooth for use in dentures for the reasons I shall outline hereinafter. In addition, I am not aware of any prior teaching of locating lugs of the type I disclose and claim herein as well as my method for using such lugs.

Another problem not contemplated by the prior art resilient artificial teeth of the type which are constructed from resilient material or the upper or lower ends of which are constructed from resilient material has to do with the use of the split metal flask by a dentist to construct dentures. In such a flask, the teeth embedded in plaster are in one half and the model of the gum ridge is placed in the other half. Plastic is mixed like putty and placed between the two halves and the flask is squeezed together. If some of the teeth are resilient, then they will be compressed. After the denture is processed and removed from the flask and pressure removed, such compressed teeth will project over the other teeth making an incorrect occlusal plane. I have solved this problem by having lip projections on the buccal (cheek) side and lingual (tongue) side of the base portion of the tooth made from the same material as the tooth. Then, when the denture is mounted in the flask and compressed, these projections will touch the plaster and prevent improper compression during processing. After removal from the flask, these lip projections or lugs are easily ground off since the denture is normally polished anyway.

Other objects and features of my present invention will become apparent as this description progresses.

To the accomplishment of the above and related objects, my invention may be embodied in the forms illustrated in the accompanying drawings, attention being called to the fact, however, that the drawings are illustrative only, and that change may be made in the specific constructions illustrated and described, so long as the scope of the appended claims is not violated.

Figure 8:
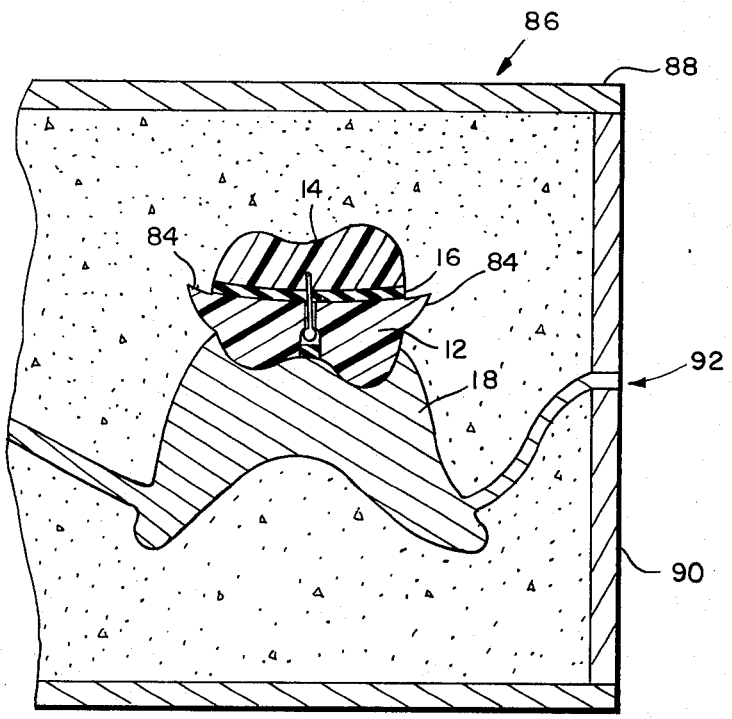
FIG. 8 is a fragmentary sectional view showing my tooth in a flask with lugs on the base portion of the tooth positioning the tooth in the dental plaster.
Figure 10:
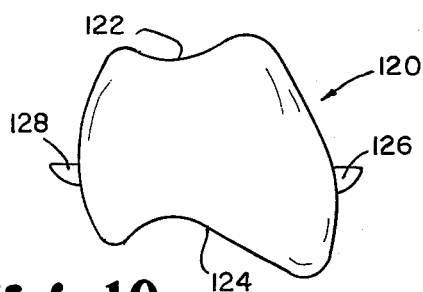
Figure 11:
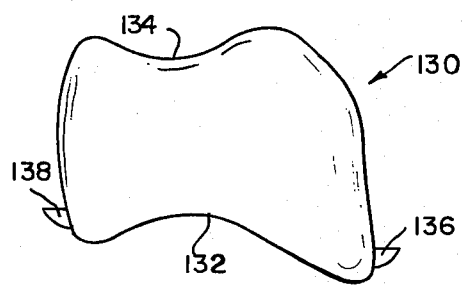
Figure 12:
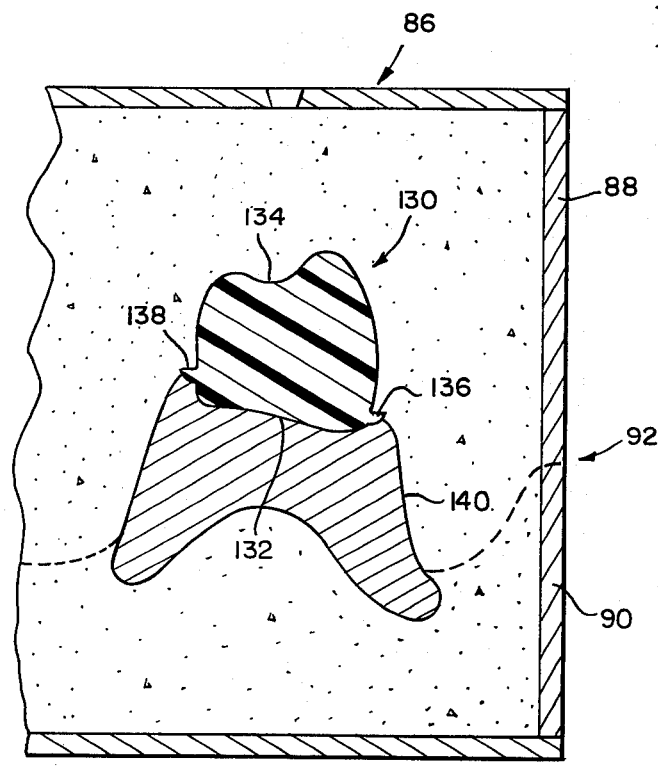
Figure 13:
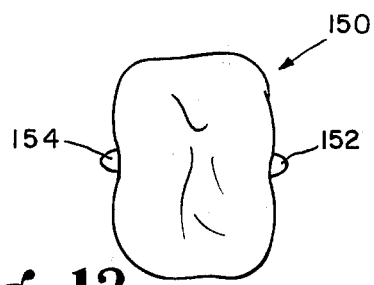
Figure 14:
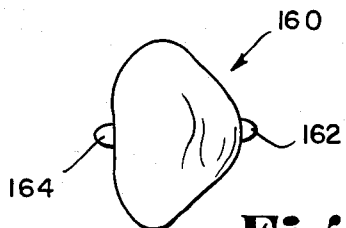
Figure 15:
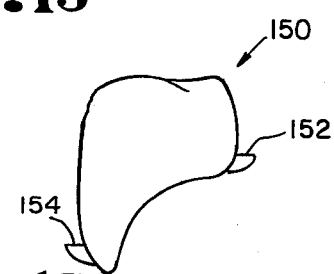
Figure 16:
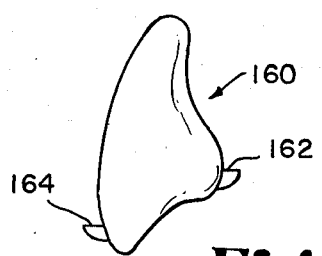

FIGS. 10 and 11 show elevational views of opposing upper and lower teeth with locating tabs extending laterally outwardly from each side (lingual or palatal and buccal or labial) with the locating lugs of FIG. 10 being nearer and occlusal surface than the ridge lap surface so as to be totally embedded in the plaster of the mold while the locating lugs of FIG. 11 are adjacent the ridge lap surface to be totally embedded in the plastic of the denture base;

FIG. 12 is a fragmentary, rather diagrammatical view, of a denture processing flask showing the separable halves similar to FIG. 8 only showing a solid artificial tooth rather than a resilient tooth;

FIGS. 13 and 14 show plan views of the occlusal surfaces of posterior denture and anterior denture teeth, respectively; and FIGS. 15 and 16 show, respectively, elevational views of the teeth shown in FIGS. 13 and 14.

Figure 1:
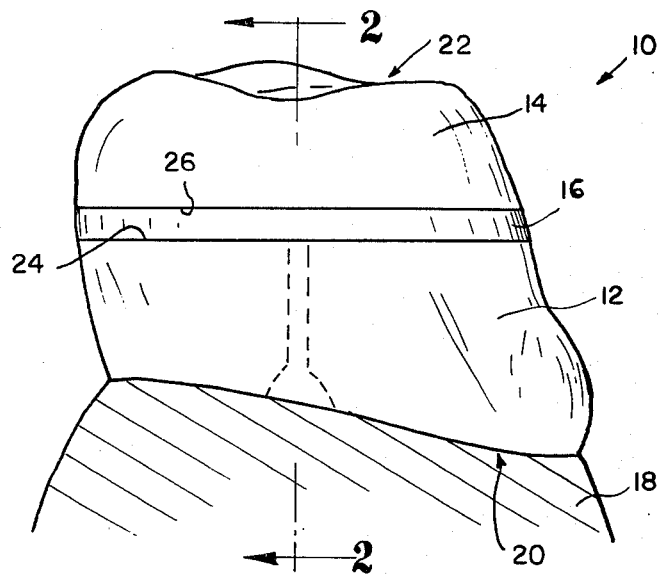
FIG. 1 is a fragmentary view of a portion of a denture showing my resiliently compressible tooth mounted thereon.
Figure 2:
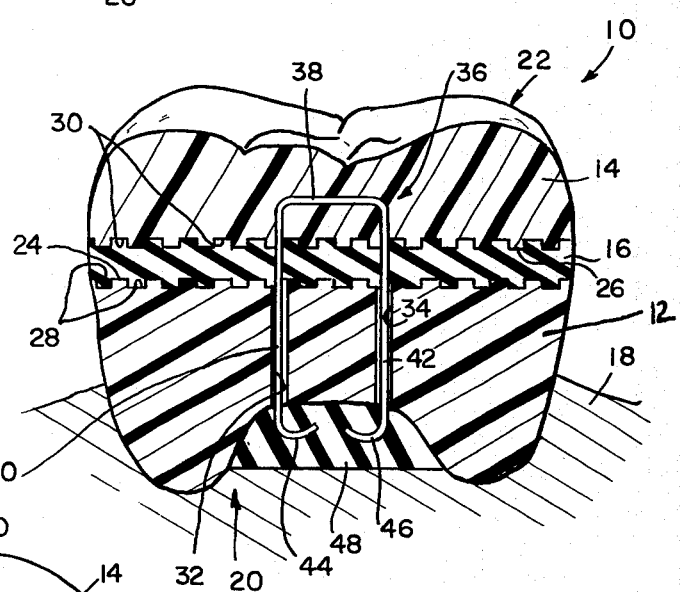
FIG. 2 is a fragmentary sectional view taken generally along the line 2—2 in FIG. 1.

Referring now to the drawings, and particularly to FIGS. 1 and 2, it will be seen that I have illustrated my artificial tooth 10 as comprising a base portion 12, an occlusal portion 14, and an intermediate resilient portion 16. The base portion 12 is mounted upon a denture base, a portion of which is indicated at 18. The reference numeral 20 indicates the ridge lap surface of the tooth while the reference numeral 22 indicates the occlusal surface of the tooth.

The intermediate portion 16 is sandwiched between the upwardly facing surface 24 provided by the base 12 and the downwardly facing surface 26 or lower surface provided by the occlusal portion 14. These surfaces 24, 26, which are preferably generally congruently superposed, lie in horizontally extending planes as bonding surfaces. In some cases, as illustrated, the bonding surfaces may be provided with small cavities or cross ridges as desired, as indicated by the reference numerals 28, 30.

Two holes 32, 34 extend vertically through the base portion 12, the holes lying in a plane which is approximately the center mesial-distal section of the tooth. Means for connecting the occusal portion 14 to the base portion 12 is indicated generally by the reference numeral 36, the illustrative means including a generally U-shaped anchor wire having a base 38 which is rigidly secured to the occlusal portion 14 and vertically downwardly extending legs 40, 42 received, respectively, in the through holes 32, 34. The distal end portions 44, 46 of the legs 40, 42 are bent inwardly or toward each other as illustrated to restrain the anchor wire from moving vertically upwardly relative to the base portion 12. It will be seen that the ridge lap surface 20 provides a well into which the portions 44, 46 extend, which well may be filled with resilient material indicated at 48 which serves to prevent the base 18 material from entering the well during the processing of the dentures. Since the holes 32, 34 are larger in diameter than the wire legs 40, 42, some tipping movement or lateral movement of the occlusal portion 14 relative to the base portion 12 is permitted. Of course, the legs 40, 42 and the end portions 44, 46 can move downwardly relative to the base portion 12 to accommodate the compression of the resilient portion 16.

Figure 3:
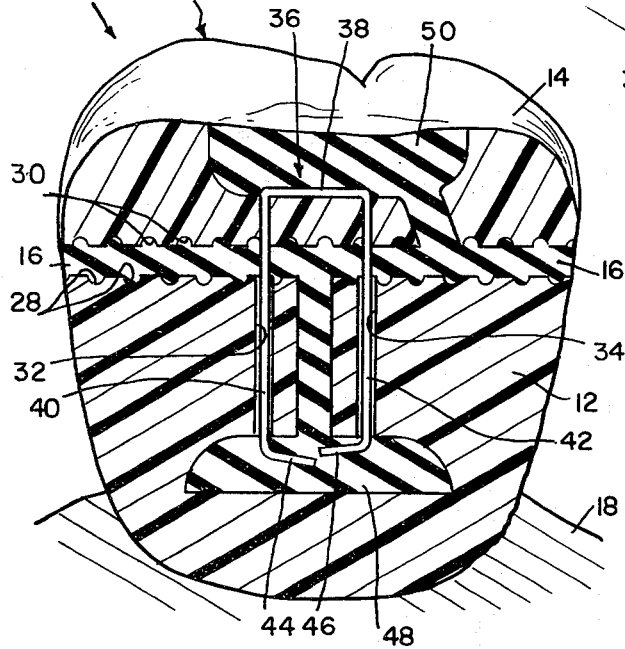
FIG. 3 is a fragmentary sectional view of another slightly different tooth in accordance with my present invention.

The embodiment of FIG. 3 indicated generally by the reference numeral 10', is very similar to the embodiment of FIGS. 1 and 2, like reference numerals representing like parts. The primary difference in the embodiment of FIG. 3 is the provision of a hollowed-out cavity 50 into which the resilient material is injected to cushion the upper or base portion 38. Thus, in the embodiment of FIG. 3, the anchor wire is not so rigidly attached to the occlusal portion 14.

I have said that the anchor wire 36 is rigidly secured to the occlusal portion 14 in FIGS. 1 and 2. This may be accomplished, for instance, by molding that occlusal portion with the wire extending into the mold. Any number of other techniques may be used rigidly to secure such an anchor wire or connector member to the occlusal portion.

Referring now to FIGS. 4–7, it will be seen that I have shown a resilient tooth indicated generally by the reference numeral 60, like reference numerals indicating like parts. One difference between the tooth 60 and the tooth 10 of FIGS. 1 and 2, is the manner in which the occlusal portion 14 is restrained from moving from its normal position away from the base portion 12. Instead of an inverted U-shaped anchor wire, there are two separate wires 40, 42 the upper ends of which are bent as indicated at 40a, 42a. Then, the distal ends of the through holes 32, 34 are enlarged as indicated at 32a, 34a to provide sockets 62, 64 in the base portion 12 for receiving the enlarged distal ends 66, 68 of the wires 40, 42. These enlarged openings 32a, 34a may preferably be plugged with a soft elastic material such as indicated at 70, 72 which prevents the hard acrylic base 18 material from flowing upwardly into the sockets 62, 64 to impede the movement of the enlarged distal ends 66, 68.

One advantage of my inventive resilient tooth is that a considerable amount of the occlusal surface 22 as well as the ridge lap surface 20 may be removed by grinding without, in any way, interfering with my mechanism for resiliently mounting the occlusal portion 14 on the base portion 12 and restraining the occlusal portion from moving away or tearing away from the base portion. The reference numerals 74, 76 indicate, respectively, the amount of occlusal surface 22 and ridge lap surface 20 which can be removed from the tooth 60. This feature applies also to the tooth 10, 10' of FIGS. 1, 2 and 3. Mass-produced teeth in accordance with my invention may be custom ground to fit a particular denture requirement.

Figure 4:
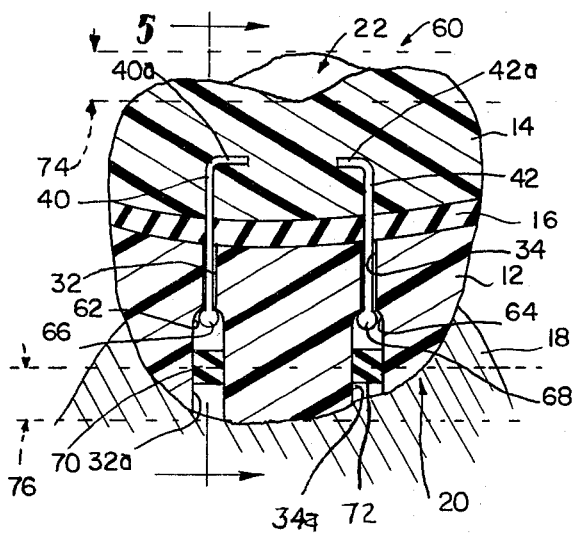
FIG. 4 is a fragmentary sectional view taken through the tooth along a vertical plane lying in the mesial-distal direction.

The sectional view of FIG. 4 is taken through a vertical plane extending centrally through the tooth in the mesial-distal direction. The two wires 40, 42 spaced apart in this plane serve to prevent the occlusal portion 14 from rotating about a vertical axis relative to the base portion 12, which rotation would be destructive to the intermediate resilient layer 16.

Figure 5:
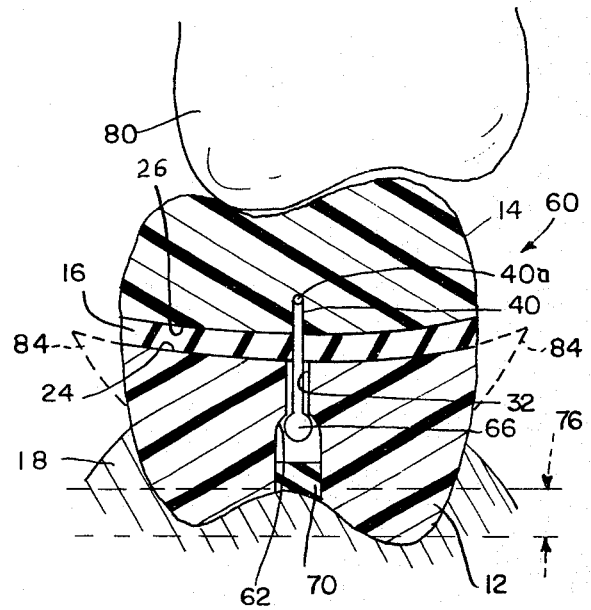
FIG. 5 is a fragmentary sectional view taken along the lines 5—5 in FIG. 4.
Figure 6:
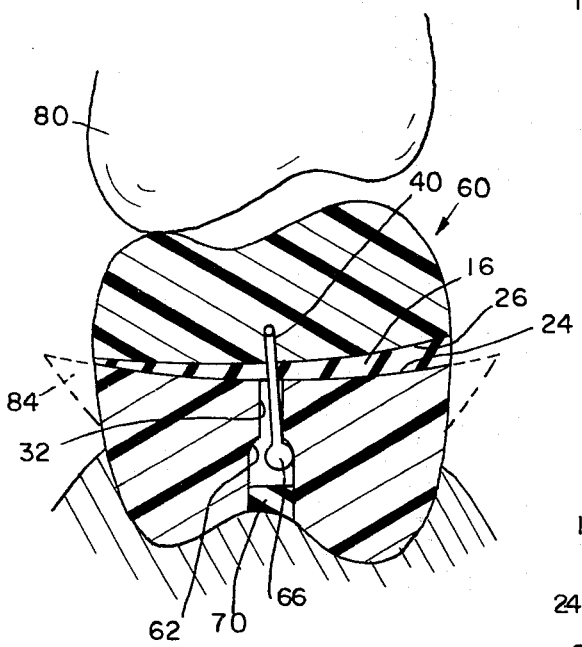
FIGS. 6 and 7 are sectional views similar to FIG. 5 but showing different tipping movement of the occlusal portion.
Figure 7:
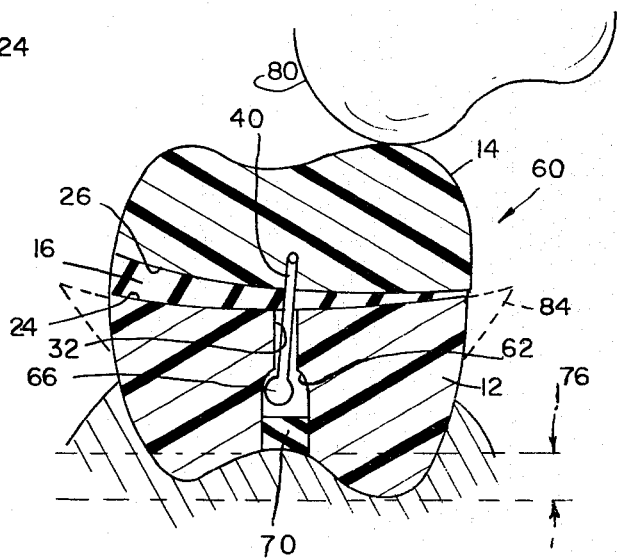

In the views 5, 6 and 7, I show an upper tooth 80 engaging the tooth 60, the views of FIGS. 5, 6 and 7 being taken in the buccal-lingual direction with the right-hand side of each view being the buccal or facial side of the left-hand side of each view being the lingual or tongue side. FIG. 5 shows the right side denture tooth 60 in occlusion with no pressure on the resilient portion 16. The retainer ball or enlarged end 66 is generally at the top of the socket 62. This position of the occlusal portion 14 represents it normal or unloaded position. It will be appreciated that the occlusal portion 14 cannot move vertically upwardly from the position of FIG. 5 because of the restraining feature of the enlarged end portion 66.

FIG. 6 shows a right lateral excursion of the mandible and lower denture with the occlusal portion 14 depressed and tipping to the lingual side. The retainer ball or enlarged end portion 66 depresses to the bottom of the socket 62 and is angulated in the over-sized hole 32. FIG. 7 shows a left lateral excursion of the mandible with the occlusal portion 14 depressed and tipping on the buccal side with the wire 40 angulated in the opposite direction relative to that shown in FIG. 6. The occlusal portion 14, therefore, can accommodate a considerable amount of excursion or grinding of the engaging occlusal surfaces of opposed teeth. The occlusal portion 14 can tip in any direction, i.e., from side to side in the buccal-lingual direction or from front to back in the mesial-distal direction.

I show laterally outwardly extending lugs or lips 84 in dashed lines on the base portion 12 of the tooth 60. These lugs 84 serve to position the base portion 12 in the dental plaster or stone of a split metal flask indicated at 86 in FIG. 8, the flask having an upper half 88 and a lower half 90. The plastic material from which the denture base 18 is made is mixed like putty and placed between the two halves 88, 90 of the flask with the parting line of the flask being indicated at 92. Then the flask is squeezed together. The lugs 84 will position themselves in the dental plaster in the flask to keep the base portion 12 from being forced against the occlusal portion 14 to place the intermediate layer 16 in compression during the squeeing process. After the denture is removed from the flask, the lugs 84 are removed by grinding and polishing operations.

Figure 9:
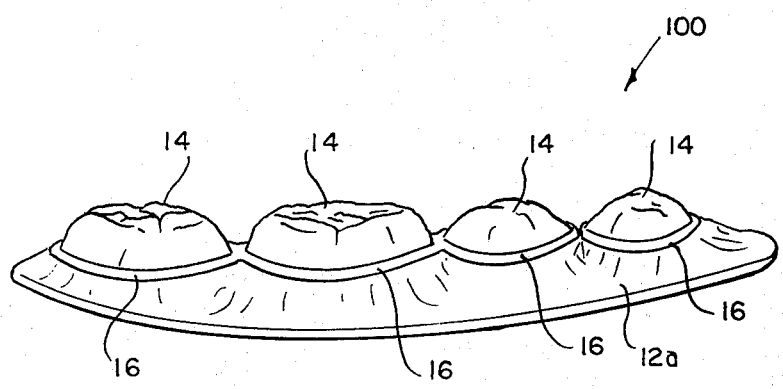
FIG. 9 is a perspective view showing a common base portion elongated in the mesial-distal direction with four occlusal portions resiliently mounted on the common base portion.

In the embodiment of FIG. 9, indicated generally at 100, four separate and individually yieldably movable occlusal portions 14 are mounted upon a common base portion 12a and resiliently supported thereon by intermediate portions 16. Each of the individual occlusal portions 14 in FIG. 9 are restrained from moving away from the base portion 12a by anchor wires such as indicated at 40, 42 in other embodiments. The entire base portion 12a, therefore, would be mounted upon a denture base 18 as an assembly.

I have shown that resilient teeth of my present invention on the lower posterior sides of the dentures. It will be appreciated that my resilient teeth may be placed upon upper denture plates as well as lower plates and even on partial denture plates.

With the above description in mind, I now turn to the advantages of my resilient tooth.

The retention mechanism (anchor wires 40, 42) is completely enclosed within the tooth to prevent deterioration in the mouth, yet the mechanism allows the necessary compressive and tipping movement of the occlusal portion 14.

I can provide the correct degree of resilience by providing intermediate portions 16 having different thicknesses. Too much resilience would result in poor occlusion and rapid deterioration of the resilient portion and the patient would not be able to bite and chew properly.

Any type of occlusal manatomy may be used as the internal fixation, i.e., anchor wires and resilient portion 16, is the same. Common occlusion is like a mortar and pestle with the pestle part being the upper and convex portion of the upper tooth while the lower part is concave.

Of prime importance is the ability of the occlusal portion 14 to tip as well as to be depressed or compressed. This prevents lateral stress on the denture base 18 and gums with consequent resorbtion of the gums.

I disclosed above the importance of precisely positioning the teeth and particularly the base portions of the teeth in the flask 86 using the lugs 84. While such positioning is very important for resilient teeth to prevent the preloading discussed, the functioning of such locating lugs 84 is also valuable in the construction of dentures having solid artificial teeth. Turning now to FIGS. 10–16, the manner in which such lugs may be placed upon teeth and used in the construction process will be discussed.

FIG. 10 shows a tooth 120 having a ridge lap surface 122, occlusal surface 124, a locating lug 126 extending out from the cheek side of the tooth and another locating lug 128 extending outwardly from the tongue side of the tooth. FIG. 11 then shows a lower tooth 130 having a ridge lap surface 132, occlusal surface 134, locating lug 136 extending outwardly from the cheek side of the tooth and a locating lug 138 extending outwardly from the tongue side of the tooth. The locating lugs 126, 128 are, perhaps, midway between the ridge lap surface 122 and occlusal surface 124 or closer to the occlusal surface 124 such that those lugs 126, 128 will be totally embedded in the plaster in the mold flask to positioning the tooth 120 and to keep the tooth from moving relative to the plaster during compression of the mold. The denture base, of course, will be formed about and to contact the ridge lap surface to be considerably above the lugs 126, 128. When the denture is removed from the mold, the lugs 126, 128 can be removed by grinding and polishing. The lugs 136, 138, however, are quite close to the ridge lap surface 132, as illustrated, such that they will be embedded in the base of the denture and left in the base of the denture. For that reason, I may find it advisable to color the lugs 136, 138 or any lugs close to the ridge lap surface the same color as the denture base. FIG. 12 shows the tooth 130 in the flask 86 in which the denture base 140 is formed.

It is not necessary, of course, for the outwardly extending locating lugs to be at the same elevation on the tooth and I have shown such different elevations in FIGS. 13–16. In FIGS. 13 and 15, I show a posterior denture tooth 150 having a locating lug 152 at one elevation on one side with a locating lug 154 at a lower elevation on the opposite side. In FIGS. 14 and 16, I show an anterior denture tooth 160 with a locating lug 162 at one elevation on one side and a locating lug 164 in a lower elevation on the opposite side.

In some cases, the locating lugs may only be partially embedded within the plastic of the denture base. If the lugs are protruding, they may be ground off when the denture is polished. Otherwise, if they are fully embedded or mostly embedded in the denture base, they may be simply left there.

Posterior denture teeth are bullet shaped and the occlusal portions of the posterior teeth are embedded in the plaster in the flask mold for processing leaving the base portion or ridge lap surface of the base portion free to contact the conventional pink plastic denture base material. A wax setup is first made in the mold in which the wax takes the place of the final pink plastic denture base for measurement purposes and the teeth can be moved if needed. Then the wax setup is embedded in the split flask in plaster. When the flask is boiled, the wax melts and can be removed and the flask 86 opened. Because of the bullet shape of the teeth, they tend to move either at this stage or in processing with the plastic, thus making the denture inaccurate (teeth in the wrong positions) when the denture is finished. There are other techniques where soft flexible material is used instead of rigid plastic, and it is even more important to have the teeth not move in such soft flexible material.

Because the teeth touch each other on the denture base, the locating lugs or tabs can only be on the buccal or labial and lingual or palatal sides.

I claim:

1. A denture comprising a denture base and a plurality of teeth anchored in said base, said base being formed in a mold in which said teeth are embedded, each said tooth having a base portion providing a ridge lap surface, an occlusal portion providing an occlusal surface, and a resilient layer sandwiched between the secured to said base portion and occlusal portion, wherein the improvement comprises lug means for locating said base portion in said mold when said base is formed, said lug means extending outwardly from said base portion to engage said mold.

2. The improvement of claim 1 in which each said tooth has a lingual or palatal side and a buccal or labial side, said lug means including a locating lug extending laterally outwardly from each side.

3. The improvement of claim 1 in which said lug means extend outwardly adjacent said ridge lap surface to be at least partially embedded in the denture base.

4. The improvement of claim 2 in which each said lug is disposed adjacent said ridge lap surface to be at least partially embedded in the denture base.

5. A denture comprising a mold cavity-formed denture base, an artificial tooth having a rigid base portion emedded in said denture base, an occlusal portion providing an occlusal surface, and a resilient layer supporting said occlusal portion on said base portion, wherein the improvement comprises lug means for locating said base portion, said lug means extending outwardly from said base portion to engage the mold in which said denture is formed and joined with said tooth.

6. The improvement of claim 5 in which said base portion provides a ridge lap surface, a buccal or labial side, and a lingual or palatal side, said lug means including, extending outwardly from each of said sides, a locating lug adjacent said ridge lap surface.

7. A method for constructing artificial dentures having a denture base and a plurality of resilient teeth embedded in said base, each said tooth including a base portion providing a ridge lap surface to be embedded in said denture base, an occlusal portion providing an occlusal surface, and a resilient layer sandwiched between and secured to said base portion and occlusal portion, said method comprising the steps of providing said plurality of said teeth, at least some of which are formed to provide, adjacent their ridge lap surfaces, outwardly extending locating lugs, embedding the occlusal portions of said teeth in a mold with said lugs engaging said mold to position the base portions relative to said occlusal portions to prevent compression of said resilient layer, forming the denture base in said mold to connect to the base portions of said teeth, removing said denture base and teeth from said mold, and then removing said lugs which are not embedded in said denture base from said teeth.

8. The method of claim 7 in which said removing step includes grinding and polishing said lugs off said teeth.

* * * * *

UNITED STATES PATENT OFFICE
CERTIFICATE OF CORRECTION

Patent No. 3,958,333        Dated May 25, 1976

Inventor(s) Henry C. Heimansohn

It is certified that error appears in the above-identified patent and that said Letters Patent are hereby corrected as shown below:

Column 4, line 64, change "squeeing" to -- squeezing --.

Column 5, line 3, "occl usal" should be -- occlusal --.

Column 5, line 37, change "disclosed" to -- discussed --.

Column 6, line 39, change "plastic" to -- plaster --.

Column 6, line 51, change "the" to -- and --.

Column 7, line 7, after "denture" insert -- base --.

Signed and Sealed this

Third Day of August 1976

[SEAL]

Attest:

RUTH C. MASON
*Attesting Officer*

C. MARSHALL DANN
*Commissioner of Patents and Trademarks*